(12) United States Patent
Lerner et al.

(10) Patent No.: US 11,911,364 B2
(45) Date of Patent: Feb. 27, 2024

(54) POSITIVE ALLOSTERIC MODULATORS OF GABA$_A$ RECEPTOR

(71) Applicant: PEPTICOM LTD., Jerusalem (IL)

(72) Inventors: Immanuel Lerner, Jerusalem (IL); Amit Michaeli, Jerusalem (IL)

(73) Assignee: PEPTICOM LTD., Jerusalum (IL)

( * ) Notice: Subject to any disclaimer, the term of this patent is extended or adjusted under 35 U.S.C. 154(b) by 224 days.

(21) Appl. No.: 17/278,393

(22) PCT Filed: Sep. 18, 2019

(86) PCT No.: PCT/IL2019/051036
§ 371 (c)(1),
(2) Date: Mar. 22, 2021

(87) PCT Pub. No.: WO2020/065642
PCT Pub. Date: Apr. 2, 2020

(65) Prior Publication Data
US 2021/0353592 A1     Nov. 18, 2021

Related U.S. Application Data

(60) Provisional application No. 62/735,983, filed on Sep. 25, 2018.

(51) Int. Cl.
*A61K 31/381* (2006.01)

(52) U.S. Cl.
CPC .................................. *A61K 31/381* (2013.01)

(58) Field of Classification Search
None
See application file for complete search history.

(56) References Cited

U.S. PATENT DOCUMENTS

| | | | |
|---|---|---|---|
| 4,814,341 A | 3/1989 | Reiter | |
| 6,218,547 B1 | 4/2001 | Teuber | |
| 6,380,210 B1 | 4/2002 | Desimone | |
| 7,425,556 B2 | 9/2008 | Chapdelaine | |
| 2004/0023993 A1 | 2/2004 | Desimone | |
| 2005/0101614 A1 | 5/2005 | Lin | |
| 2010/0137676 A1 | 6/2010 | Goldstein | |
| 2012/0083599 A1 | 4/2012 | Thomas | |
| 2012/0094837 A1 | 4/2012 | Muehlthau | |

FOREIGN PATENT DOCUMENTS

| | | |
|---|---|---|
| EP | 2557088 B1 | 5/2016 |
| WO | 2013149336 A1 | 10/2013 |
| WO | 2017141248 A1 | 8/2017 |

OTHER PUBLICATIONS

PubChem Record: Compound CID 51090838 (create date: May 3, 2011).*
Chung et al., (2010) Structure-activity analysis of vinylogous urea inhibitors of human immunodeficiency virus-encoded ribonuclease H. Antimicrob Agents Chemother 54(9): 3913-3921.
Cornell et al., (1995) A Second Generation Force Field for the Simulation of Proteins, Nucleic Acids, and Organic Molecules. J Am Chem Soc 117(19): 5179-5197.
Froese et al., (2015) Structural basis of glycogen branching enzyme deficiency and pharmacologic rescue by rational beptide design. Hum Mol Genet 24(20): 5667-5676.
Gou et al., (2012) Evolution of neurotransmitter gamma-aminobutyric acid, glutamate and their receptors. Dongwuxue Yanjiu 33(E5-6): E75-E81.
Jembrek and Vlainic (2015) GABA Receptors: Pharmacological Potential and Pitfalls. Current pharmaceutical design. 21. 10.2174/1381612821666150914121624; 59 pages.
Michaeli et al., (2020) Discovery of Novel GABAAR Allosteric Modulators Through Reinforcement Learning. Current Pharmaceutical Design; DOI: 10.2174/1381612826666201113104150. 7 pages.
Pubchem, Compound Summary for SID 334824269. Available Date: Apr. 25, 2017 [retrieved on Feb. 6, 2020]. Retrieve from the Internet: <URL: https://pubchem.ncbi.nlm.nih.gov/substance/334824269> entire document.

* cited by examiner

*Primary Examiner* — Bong-Sook Baek
(74) *Attorney, Agent, or Firm* — RAPHAEL BELLUM PLLC

(57) ABSTRACT

The present invention provides new GABA$_A$ receptor-binding compounds that modify the activation of GABA$_A$, their use in the preparation of a neuroactive pharmaceutical composition, improving sperm motility and labeling of biomolecules.

4 Claims, 2 Drawing Sheets

Compound 1

Results, n=4:

| Application | Peak current modulation (%) | Mean ± SD (% n=4) |
|---|---|---|
| 1 µM | -13.48, -19.75, -12.52, -5.18 | -12.73 ± 5.97% |
| 10 µM | -11.05, -2.65, -8.37, -1.33 | -5.85 ± 4.62% |
| 30 µM | 72.46, 96.50, 57.50, 65.46 | 72.98 ± 16.83% |
| 100 µM | 254.82, 280.10, 211.82, 227.80 | 243.64 ± 30.10% |
| 300 µM | 548.22, 333.31, 447.59, 449.32 | 444.61 ± 87.85% |
| Wash out 1 (2 µM GABA) | -22.34, 6.12, -12.86, 10.45 | -4.65 ± 15.54% |
| Wash out 2 (2 µM GABA) | -26.67, 3.54, -19.90, 7.58 | -8.87 ± 16.96% |
| Positive Control (500 µM Pentobarbital) | 133.79, 304.86, 201.22, 413.96 | 263.46 ± 122.55% |

GABA 2 µM —
Positive control 500 µM ·····

Compound 2

Results, n=3:

| Application | Peak current modulation (%) | Mean ± SD (% n=3) |
|---|---|---|
| 1 μM | -36.86, -11.14, -32.25 | -26.75 ± 13.71 |
| 10 μM | -56.94, -45.19, -60.41 | -54.18 ± 7.98 |
| 30 μM | -82.09, -67.68, -85.40 | -78.39 ± 9.42 |
| 100 μM | -95.49, -85.17, -93.62 | -91.43 ± 5.50 |
| 300 μM | -99.91, -95.17, -97.87 | -97.65 ± 2.38 |
| Wash out 1 (2 μM GABA) | 23.29, -5.22, 7.85 | 8.64 ± 14.27 |
| Wash out 2 (2 μM GABA) | 29.27, -3.50, 15.81 | 13.86 ± 16.47 |
| Positive Control (500 μM Pentobarbital) | 179.67, 183.05, 346.67 | 236.46 ± 95.46 |

GABA 2 μM

Positive control 500 μM

POSITIVE ALLOSTERIC MODULATORS OF GABA$_A$ RECEPTOR

TECHNICAL FIELD

The present invention relates to the field of neuroscience, and more particularly, to compounds that modify the activation of the human γ-aminobutyric acid receptor A (GABA$_A$ receptor).

BACKGROUND

GABA is the main inhibitory neurotransmitter in both vertebrate and invertebrate organisms (Gou et al. 2012, *Evolution of neurotransmitter gamma-aminobutyric acid, glutamate and their receptors*, Dongwuxue Yanjiu. 33(E5-6): E75-81). GABA receptors are divided into two major classes: the GABA$_A$ ionotropic Cl-channels and the G protein-coupled GABA$_B$ receptors. GABA$_A$ receptors play a crucial role in the central nervous system (CNS) in homeostasis and pathological conditions, such as anxiety disorder, epilepsy, insomnia, spasticity, aggressive behavior, and other pathophysiological conditions and diseases (Jemberk et al. 2015, *GABA Receptors: Pharmacological Potential and Pitfalls*, Current Pharmaceutical Design 21, 4943-59). GABA receptors have been linked to physiological activity outside of the nervous system, in roles like modulation of sperm motility and others.

U.S. Pat. No. 6,380,210 B1 describes substituted heteroaryl fused aminoalkyl-imidazole derivatives acting as selective modulators of GABA$_A$ receptors and their use in enhancing alertness and treating anxiety, overdoses of benzodiazepine-type drugs, Down syndrome, depression, sleep, seizure and cognitive disorders both in human as well as domestic pets and livestock. U.S. Pat. No. 6,218,547 B1 discloses 1-phenyl-benzimidazole derivatives also acting as GABA$_A$ receptor modulators and used to treat the CNS-related disorders, such as anxiety, anesthesia, epilepsy, or convulsions in humans and animals.

U.S. Pat. No. 7,425,556 B1 discloses a number of cinnoline compounds including some selected 4-amino- and 4-oxo-cinnoline-3-carboxamides capable of modulating activity of the GABA$_A$ receptor and used as medicaments for treating or preventing an anxiety disorder, cognitive disorder, or mood disorder. US 2005/0101614 A1 describes a number of heterocyclic GABA$_A$-subtype selective receptor modulators selected from substituted derivatives of 7-arylindazole, 7-aryl-2H-pyrazolo[3,4-c]pyridine, 7-aryl-2H-pyrazolo[4,3-c]pyridine and 7-aryl-2H-pyrazolo[4,3-b]pyridine compounds.

However, none of the prior art publications discloses or suggests the novel compounds of the present invention or suggests their use as CNS depressants. The compounds of the present invention were tested and validated as positive allosteric modulators or specific inhibitors of the human $\alpha_1\beta_3\gamma_2$ GABA$_A$ receptor. The discovered compounds have a strong effect on any physiological/pathological process involving the activity of GABA$_A$ receptor, including but not limited to anxiolytic, sedative, and hypnotic effects as well as non-neurological roles such as modulation of sperm activity.

SUMMARY

In one aspect, the present invention provides GABA$_A$ receptor-binding compounds of Formula IA and IB:

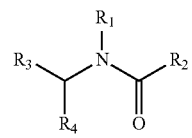

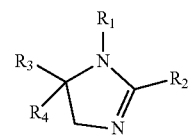

wherein R$_1$ is H or methyl;
R$_2$ is furanyl, 1H-pyrrolyl, imidazolyl, thiophenyl, oxazolyl, thiazolyl, or 1,3,4-thiadiazolyl, optionally substituted at any available carbon atom of said heteroaromatic ring with (C$_1$-C$_3$)alkyl or sulphonamide group;
R$_3$ is (C$_1$-C$_3$)alkyl, hydroxyl or ammonium group; and
R$_4$ is thiophenyl, furanyl, 1H-pyrrolyl, imidazolyl, oxazolyl, thiazolyl, or 1,3,4-thiadiazolyl, optionally substituted at any available carbon atom of said heteroaromatic ring with hydroxyl or (C$_1$-C$_3$)alkyl group.

In another aspect, the present invention provides GABA$_A$ receptor-binding compounds of Formula II:

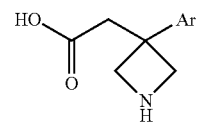

wherein Ar is phenyl, benzyl, pyrimidinyl, pyridazinyl, 1,3,5-triazinyl or pyrazinyl, optionally substituted at any available carbon atom of said aromatic or heteroaromatic ring with (C$_1$-C$_3$)alkyl, hydroxyl or halogen group.

All the compounds of the present invention were tested and validated using electrophysiological recordings on the human GABA$_A$ receptor comprising of the following subunits $\alpha_1\beta_3\gamma_2$. The compounds of the present invention are used in the preparation of a neuroactive pharmaceutical composition, in improving sperm motility or in labeling of biomolecules.

Various embodiments may allow various benefits, and may be used in conjunction with various applications. The details of one or more embodiments are set forth in the accompanying figures and the description below. Other features, objects and advantages of the described techniques will be apparent from the description and drawings and from the claims.

BRIEF DESCRIPTION OF THE DRAWINGS

Disclosed aspects of the present invention will be understood and appreciated more fully from the following detailed description taken in conjunction with the appended figures. The drawings included and described herein are schematic and are not limiting the scope of the disclosure.

DETAILED DESCRIPTION

Figure 1:
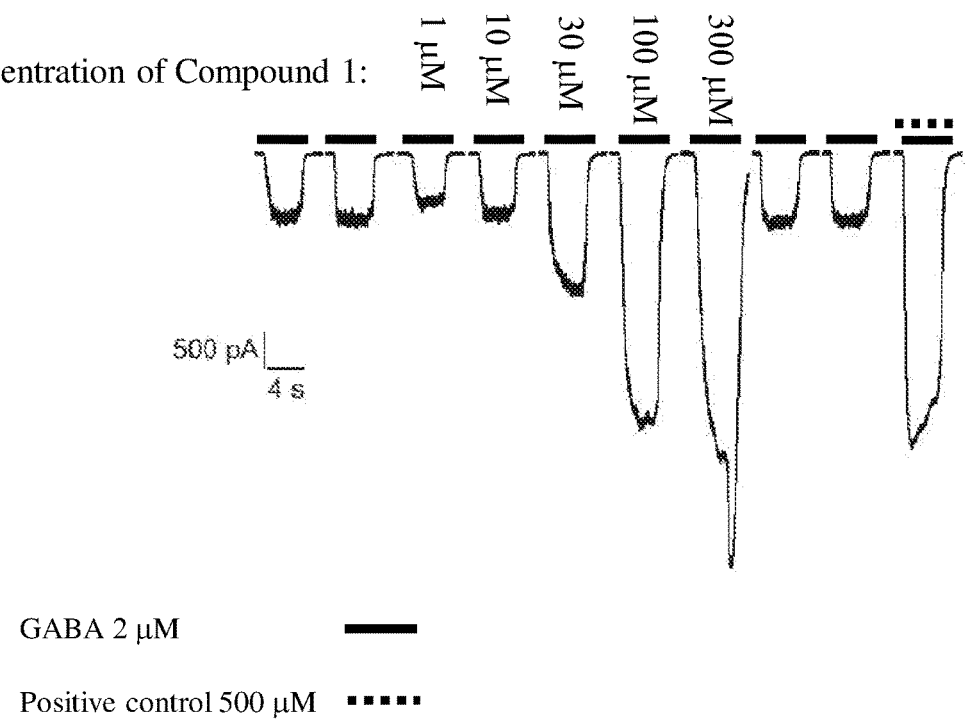
FIG. 1 shows selective potentiation of human GABA receptor-mediated Cl$^-$ current by Compound 1. The human GABA receptor (subunits $\alpha_1\beta_3\gamma_2$) was expressed in HEK293 cells in manual whole-cell patch-clamp settings.

In the following description, various aspects of the present application will be described. For purposes of explanation, specific configurations and details are set forth in order to provide a thorough understanding of the present application. However, it will also be apparent to one skilled in the art that the present application may be practiced without the specific details presented herein. Furthermore, well-known features may be omitted or simplified in order not to obscure the present application.

The term "comprising", used in the claims, is "open ended" and means the elements recited, or their equivalent in structure or function, plus any other element or elements which are not recited. It should not be interpreted as being restricted to the means listed thereafter; it does not exclude other elements or steps. It needs to be interpreted as specifying the presence of the stated features, integers, steps or components as referred to, but does not preclude the presence or addition of one or more other features, integers, steps or components, or groups thereof. Thus, the scope of the expression "a compound comprising x and z" should not be limited to compounds consisting only of moieties or groups x and z. Also, the scope of the expression "a method comprising the steps x and z" should not be limited to methods consisting only of these steps.

Unless specifically stated, as used herein, the term "about" is understood as within a range of normal tolerance in the art, for example within two standard deviations of the mean. In one embodiment, the term "about" means within 10% of the reported numerical value of the number with which it is being used, preferably within 5% of the reported numerical value. For example, the term "about" can be immediately understood as within 10%, 9%, 8%, 7%, 6%, 5%, 4%, 3%, 2%, 1%, 0.5%, 0.1%, 0.05%, or 0.01% of the stated value. In other embodiments, the term "about" can mean a higher tolerance of variation depending on for instance the experimental technique used. Said variations of a specified value are understood by the skilled person and are within the context of the present invention. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges, for example from 1-3, from 2-4, and from 3-5, as well as 1, 2, 3, 4, 5, or 6, individually. This same principle applies to ranges reciting only one numerical value as a minimum or a maximum. Unless otherwise clear from context, all numerical values provided herein are modified by the term "about". Other similar terms, such as "substantially", "generally", "up to" and the like are to be construed as modifying a term or value such that it is not an absolute. Such terms will be defined by the circumstances and the terms that they modify as those terms are understood by those of skill in the art. This includes, at very least, the degree of expected experimental error, technical error and instrumental error for a given experiment, technique or an instrument used to measure a value.

As used herein, the term "and/or" includes any and all combinations of one or more of the associated listed items. Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element or atom is referred to as being "attached to", "connected to" etc., another element or atom, it can be attached to or connected to the other element or atom, or intervening elements or atoms may also be present. It will also be appreciated by those of skill in the art that references to a structure or feature that is disposed "adjacent" another feature may have portions that overlap or underlie the adjacent feature.

In one aspect, the present invention provides a $GABA_A$ receptor-binding compound of Formula IA or IB:

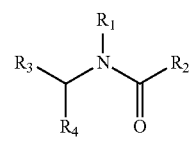

IA

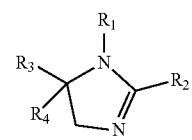

IB wherein $R_1$ is H or methyl;

$R_2$ is furanyl, 1H-pyrrolyl, imidazolyl, thiophenyl, oxazolyl, thiazolyl, or 1,3,4-thiadiazolyl, optionally substituted at any available carbon atom of said heteroaromatic ring with $(C_1-C_3)$alkyl or sulphonamide group;

$R_3$ is $(C_1-C_6)$alkyl, hydroxyl or ammonium group; and $R_4$ is thiophenyl, furanyl, 1H-pyrrolyl, imidazolyl, oxazolyl, thiazolyl, or 1,3,4-thiadiazolyl, optionally substituted at any available carbon atom of said heteroaromatic ring with hydroxyl or $(C_1-C_3)$alkyl group.

The above substitution pattern of the compounds of Formulae IA and IB was found to be compatible with $GABA_A$-R activity. An exemplary compound of Formula IA exhibiting positive allosteric modulation of the human $GABA_A$ receptor is Compound 1 of the following formula:

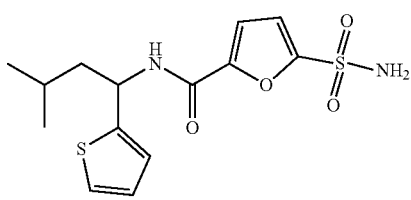 [SMILES: CC(C)CC(NC(=O)c1ccc(S(N)(=O)=O)o1)c1cccs1]

In yet further aspect, the present invention provides a $GABA_A$ receptor-binding compound of Formula II:

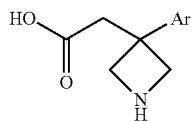

II wherein Ar is phenyl, benzyl, pyrimidinyl, pyridazinyl, 1,3,5-triazinyl or pyrazinyl, optionally substituted at any available carbon atom of said aromatic or heteroaromatic ring with ($C_1$-$C_3$)alkyl, hydroxyl or halogen group.

The above substitution pattern of the compounds of Formula II was found to be compatible with $GABA_A$-R activity. An exemplary compound of Formula II inhibiting the human $GABA_A$ receptor is Compound 2 of the following formula:

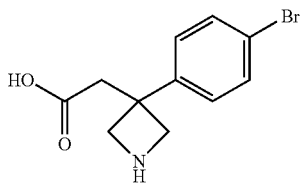 [SMILES: O=C(O)CC1(c2ccc(Br)cc2)CNC1]

Figure 2:
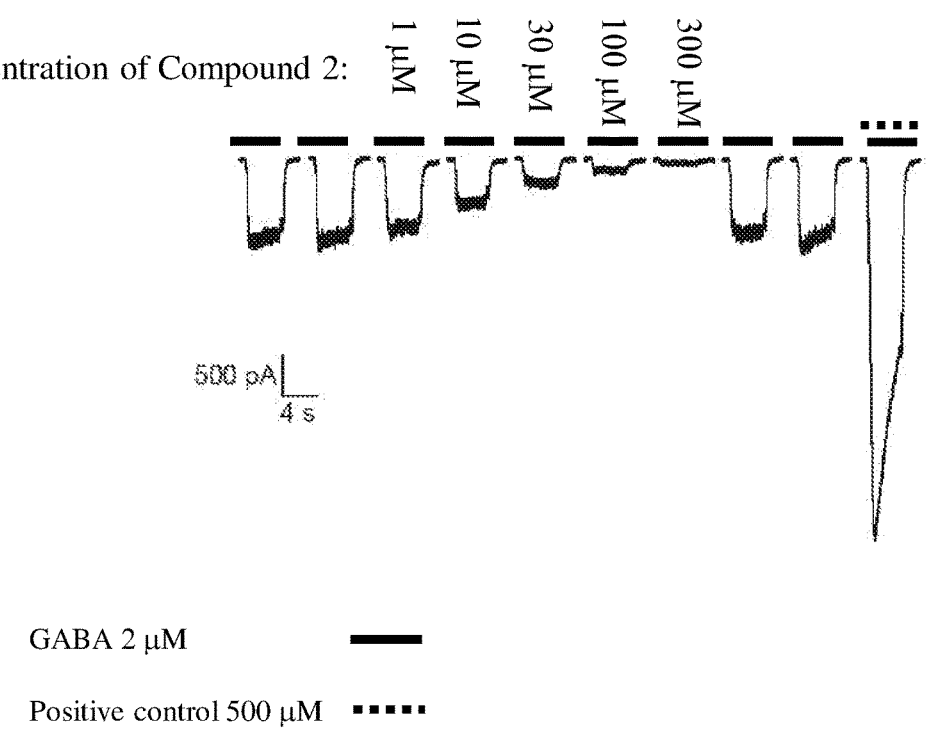
FIG. 2 shows selective potentiation of human GABA receptor-mediated Cl$^-$ current by Compound 2. The human GABA receptor (subunits $\alpha_1\beta_3\gamma_2$) was expressed in HEK293 cells in manual whole-cell patch-clamp settings.

These compounds of the present invention are experimentally shown to specifically bind to the $GABA_A$ receptor. Therefore, they are capable of activating, inhibiting or modulating the $GABA_A$ receptor. These compounds were derived in-silico and tested in-vitro in cell cultures. FIGS. 1 and 2 demonstrate the selective potentiation of the human GABA receptor-mediated $Cl^-$ current by Compounds 1 and 2, respectively. The human GABA receptor (subunits $\alpha_1\beta_3\gamma_2$) used in these experiments was expressed in the HEK293 cells in manual whole-cell patch-clamp settings.

In another aspect, the compounds of the present invention are used for the preparation of neuroactive or psychoactive compositions, such as anti-depressants, anti-addictive or anti-epileptic drugs, or any other medical compositions, which are capable of exhibiting the $GABA_A$ receptor modulation.

Specific combinations of the compounds of the present invention may be selected with respect to delivery considerations of the compounds to the target tissue, e.g., with respect to their solubility and biological interactions that may be determined experimentally along the lines exemplified herein for specific examples.

In certain embodiments, possible applications of the compounds of the present invention or their molecular derivatives are in the pharmaceutical industry as drugs for any relevant clinical indication with a need to modify $GABA_A$ receptor activity. They may also be used in a wide variety of clinical applications, as well as in diagnostics and imaging applications. Non-limiting examples of using these compounds comprise protection from anti-depressants and anti-addictive indications. They may also be used for fluorescent or non-fluorescent biolabeling in the process of modulating and binding the $GABA_A$ receptor for experimental use, in in-vitro or in-vivo, and as specific inhibitors for basic research (in neuroscience).

Examples

Calculation of the Binding Energy Contributions

The binding energy contributions were calculated using an ab initio algorithm that takes into account molecular mechanics force-fields in 3D (three dimensional) space and at a 1 Å resolution. The binding energy contributions were calculated using the Assisted Model Building with Energy Refinement (AMBER) (Cornell 1995, *A Second Generation Force Field for the Simulation of Proteins*, Nucleic Acids, and Organic Molecules. Journal of the American Chemical Society 117, 5179-97). It was force-field with the Generalized-Born/Surface Area (GB/SA) solvation model, and was already effectively applied to other fields as well (Froese et al. 2015, *Structural basis of glycogen branching enzyme deficiency and pharmacologic rescue by rational peptide design*, Human Molecular Genetics 24(20), 5667-5676). The obtained data on the binding energy contributions can be used to design the $GABA_A$-binding compounds, e.g., incorporate the compounds into proteins or modify their structure while maintaining the overall negative binding energy.

While certain features of the present application have been illustrated and described herein, many modifications, substitutions, changes, and equivalents will be apparent to those of ordinary skill in the art. It is, therefore, to be understood that the appended claims are intended to cover all such modifications and changes as fall within the true spirit of the present application.

The invention claimed is:

1. A method of treating depression, addiction or epilepsy, the method comprising administering to a subject in need thereof a $GABA_A$ receptor-binding compound of the following formula (Compound 1):

2. The method according to claim 1, for treating depression.

3. The method according to claim 1, for treating addiction.

4. The method according to claim 1, for treating epilepsy.

* * * * *